(12) United States Patent
Kim et al.

(10) Patent No.: US 10,517,913 B2
(45) Date of Patent: Dec. 31, 2019

(54) COMPOSITION FOR PREVENTION, ALLEVIATION, OR TREATMENT OF PERIPHERAL NEUROPATHY COMPRISING LITHOSPERMI RADIX EXTRACT AS AN EFFECTIVE COMPONENT

(71) Applicant: KOREA INSTITUTE OF ORIENTAL MEDICINE, Daejeon (KR)

(72) Inventors: No Soo Kim, Daejeon (KR); Jong-Shik Park, Sejong-si (KR); Jin-Mu Yi, Chungcheongbuk-do (KR); You Jin Lee, Daejeon (KR); Eun-Sang Cho, Daejeon (KR); Jinhee Kim, Daejeon (KR); Chae Jun Lim, Gwangju (KR); Ok-Sun Bang, Daejeon (KR); Youngah Kim, Daegu (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 173 days.

(21) Appl. No.: 15/572,062

(22) PCT Filed: Sep. 30, 2015

(86) PCT No.: PCT/KR2015/010333
§ 371 (c)(1),
(2) Date: Nov. 6, 2017

(87) PCT Pub. No.: WO2016/182139
PCT Pub. Date: Nov. 17, 2016

(65) Prior Publication Data
US 2018/0303889 A1    Oct. 25, 2018

(30) Foreign Application Priority Data

May 12, 2015    (KR) .................... 10-2015-0065825

(51) Int. Cl.
*A61K 36/30*     (2006.01)
*A61K 31/282*    (2006.01)
*A61K 31/337*    (2006.01)
*A61P 25/02*     (2006.01)

(52) U.S. Cl.
CPC ............ *A61K 36/30* (2013.01); *A61K 31/282* (2013.01); *A61K 31/337* (2013.01); *A61P 25/02* (2018.01); *A61K 2300/00* (2013.01)

(58) Field of Classification Search
None
See application file for complete search history.

(56) References Cited

FOREIGN PATENT DOCUMENTS

| | | | |
|---|---|---|---|
| CN | 104398774 A | * | 3/2015 |
| JP | 2014108931 A | | 6/2014 |
| KR | 10-0558159 B1 | | 3/2006 |
| KR | 10-2006-0064068 | | 6/2006 |
| KR | 10-2015-0047173 A | | 5/2015 |
| WO | WO 2013/025004 A2 | | 2/2013 |

OTHER PUBLICATIONS

European Search Report for EP15891955.5 dated Nov. 27, 2018 from European patent office in a counterpart European patent application.
International Search Report for PCT/KR2015/010333, dated Jan. 25, 2016.
Jin, R. et al, "Immunomodulative Effects of Chinese Herbs in Mice Treated with Anti-tumor Agent Cyclophosphamide", Yakugaku Zasshi (Journal of the Pharmaceutical Society of Japan), vol. 114, No. 7, pp. 533-538, 1994 (English Abstract is submitted herewith).
Rajasekar, S. et al., "In vitro and in vivo anticancer effects of Lithospermum erythrorhizon extract on B16F10 murine melanoma", Journal of Ethnopharmacology, vol. 144, pp. 335-345, 2012.
Kyu Yeon Han et al., "Suppressive effects of Lithospermum erythrorhizon extracts on lipopolysaccharide-induced activation of AP-1 and NF-κB via mitogen-activated protein kinase pathways in mouse macrophage cells", BMB reports, vol. 41(4), pp. 328-333, 2008.
Chia-Yen Hsiao et al., "TheMolecular Basis of Wound Healing Processes Induced by Lithospermi Radix: A Proteomics and Biochemical Analysis", Evidence-Based Complementary and Alternative Medicine, vol. 2012, pp. 1-15, 2012.
Eun Kyoung Kim et al., "Lithospermi radix Extract Inhibits Histamine Release and Production of Inflammatory Cytokine in Mast Cells", Bioscience, Biotechnology, and Biochemistry., vol. 71 (12), pp. 2886-2892, 2007.
Richard A C Hughes, "Peripheral neuropathy", BMJ, vol. 324, No. 23, pp. 466-469, Feb. 2002.
Janet M. Torpy, "Peripheral Neuropathy", JAMA, vol. 303, No. 15, Apr. 21, 2010.
Anjali Bhagra et al., "Chemotherapy-induced Neuropathy", Current Oncology Report, vol. 9, pp. 290-299, 2007.

(Continued)

*Primary Examiner* — Susan Hoffman
(74) *Attorney, Agent, or Firm* — The PL Law Group, PLLC

(57) ABSTRACT

A composition comprising a Lithospermi Radix extract as an effective component prevents, alleviates, or treats peripheral neuropathy, in particular, peripheral neuropathy induced by an anti-cancer agent (i.e., chemotherapy-induced peripheral neuropathy). A method for preventing or treating peripheral neuropathy includes administering to a subject in need thereof the composition. The Lithospermi Radix extract can relieve the suppressed growth of neurites caused by an anti-cancer agent while neither inducing any cytotoxicity in normal cells nor changing the unique cytotoxic potential of an anti-cancer agent in human cancer cells. In addition, the Lithospermi Radix extract can efficiently lower the enhanced sensitivity to painful stimuli in peripheral neuropathic animals induced by an anti-cancer agent. Thus, the Lithospermi Radix extract can be advantageously used as an effective component of a composition for prevention, alleviation, or treatment of chemotherapy-induced peripheral neuropathy.

16 Claims, 9 Drawing Sheets

Specification includes a Sequence Listing.

(56) References Cited

OTHER PUBLICATIONS

Terri Armstrong et al., "Chemotherapy-Induced Peripheral Neuropathy", Oncology Nursing Forum, vol. 32, No. 2, pp. 305-311, 2005.
Constance Visovsky et al., "Evaluation and Management of Peripheral Neuropathy in Diabetic Patients With Cancer", Clinical Journal of Oncology Nursing, vol. 12, No. 2, pp. 243-247, 2008.
Guido Cavaletti et al., "Chemotherapy-Induced Neuropathy", Current Treatment Options in Neurology vol. 13 pp. 180-190, 2011.
Lorenzo Di Cesare Mannelli et al., "Morphologic Features and Glial Activation in Rat Oxaliplatin-Dependent Neuropathic Pain", The Journal of Pain, vol. 14, No. 12, pp. 1585-1600, 2013.

\* cited by examiner a: (-) NGF
b: (+) NGF
c: (+) NGF + Oxal + V
d: (+) NGF + Oxal + Ami
e: (+) NGF + Oxal + WLR(25)
f: (+) NGF + Oxal + WLR(100)

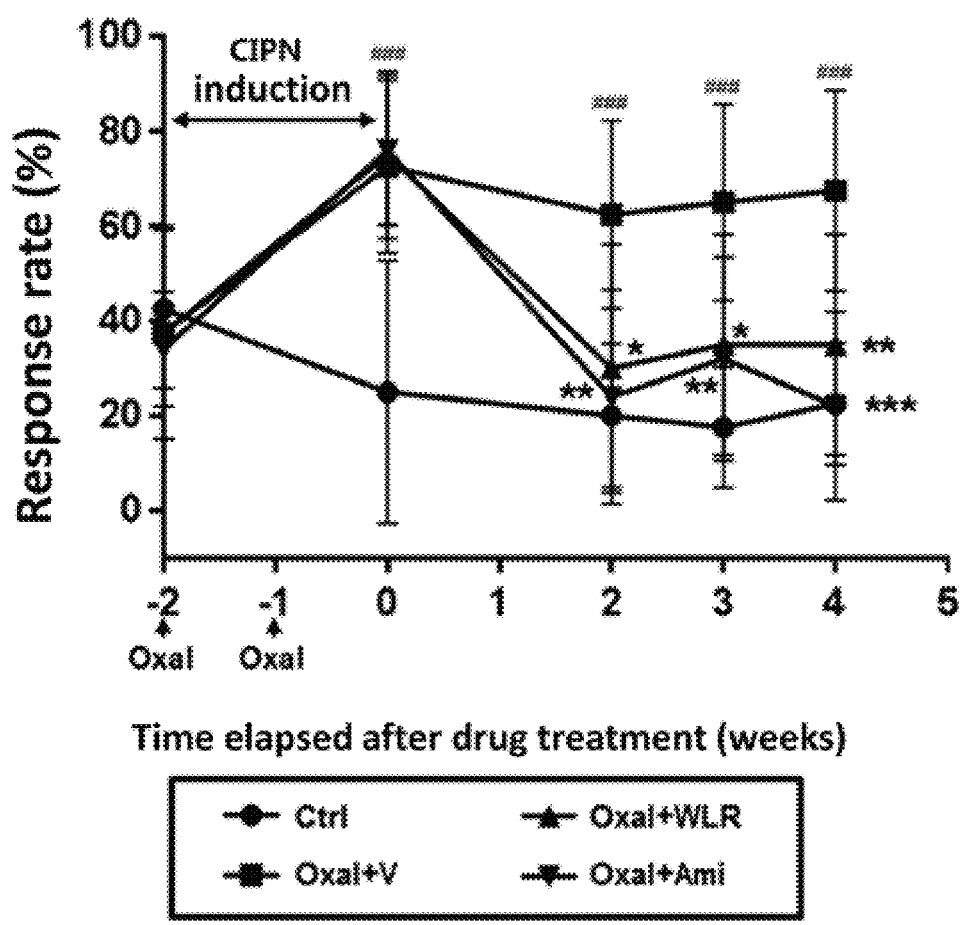

Fig.6
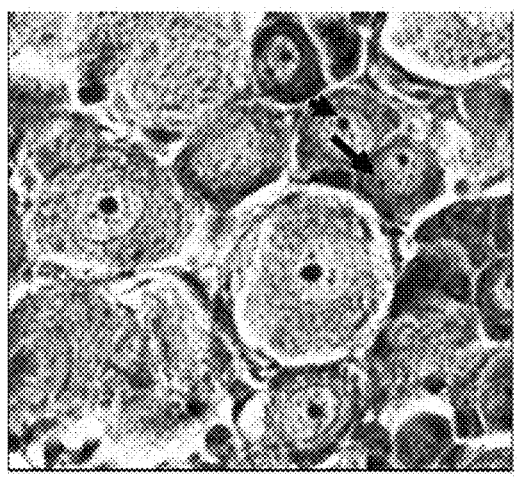
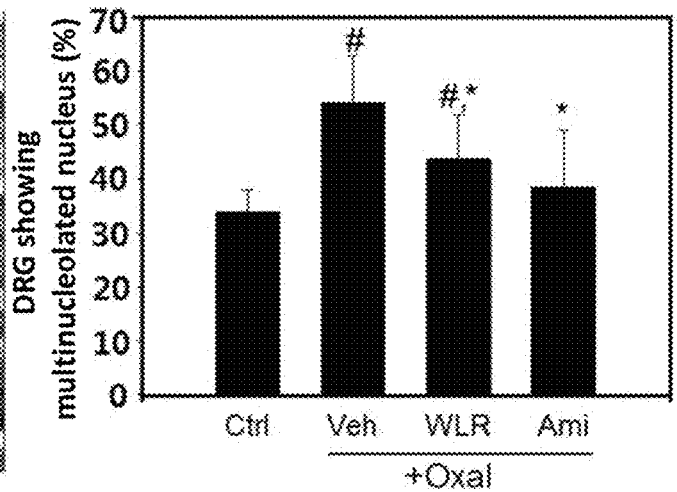
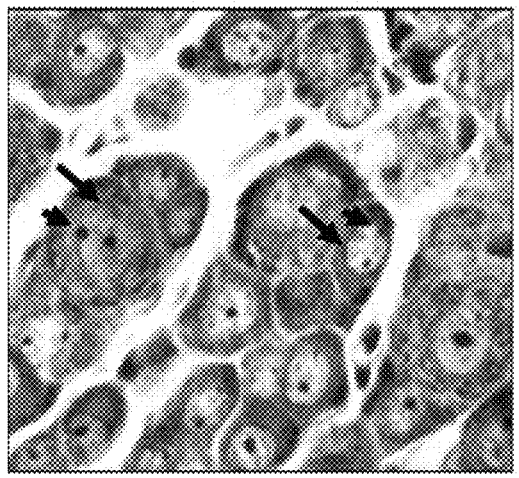
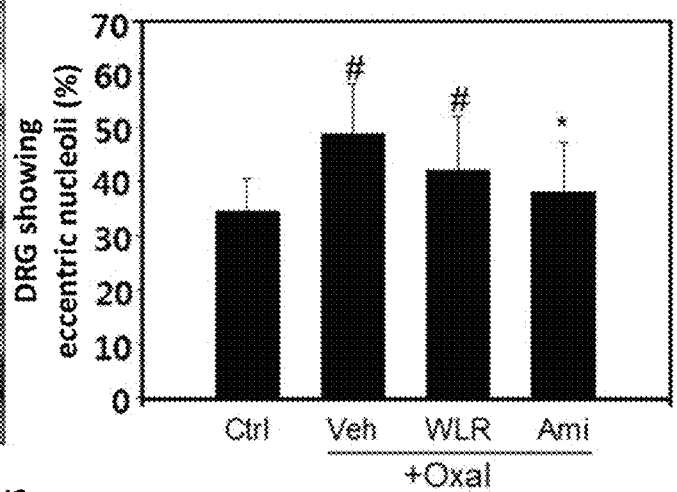
→ Multinucleolated nucleus
→ Eccentric nucleoli ic # COMPOSITION FOR PREVENTION, ALLEVIATION, OR TREATMENT OF PERIPHERAL NEUROPATHY COMPRISING LITHOSPERMI RADIX EXTRACT AS AN EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/010333, filed Sep. 30, 2015, which claims priority to the benefit of Korean Patent Application No. 10-2015-0065825 filed in the Korean Intellectual Property Office on May 12, 2015, the entire contents of which are incorporated herein by reference.

TECHNICAL FIELD

The present invention relates to a composition for prevention, alleviation, or treatment of peripheral neuropathy comprising a Lithospermi Radix extract as an effective component.

BACKGROUND ART

An occurrence of peripheral neuropathy is caused by a disorder which provides damage directly on neural tissues or affects neural tissues. Depending on the type of neural tissues that are affected, peripheral neuropathy can be categorized into sensory neuropathy, motor neuropathy, and autonomic neuropathy. In case of sensory neuropathy, a patient may feel numbness to touch, shaking, a reduced ability to sense temperature change, tingling feeling, or burning pain, and also skin allodynia or the like. Meanwhile, motor neuropathy is accompanied with impaired balance, weakness of muscle strength, and a patient with autonomic neuropathy experiences, depending on an organ affected by corresponding neuron, urinary incontinence due to weakened bladder controlling activity, or has abnormal blood pressure and heartbeat (R. A. Hughes, 2002, BMJ, v324, pp 466-469; J. M. Torpy et al., 2010, JAMA, v303, p 1556).

Various factors have been suggested as a cause of peripheral neuropathy, such as genetic disorders, metabolic or endocrine disorders, inflammatory disorders, malnutrition like vitamin deficiency, and anti-cancer agents administered during cancer treatment. Among them, chemotherapy-induced peripheral neuropathy (CIPN) is an adverse side effect that may reduce the dosage of the anti-cancer agent administered to a patient depending on severity of symptoms or, in an extreme case, may early terminate the anti-cancer therapy, which negatively affect anti-cancer therapy. It is known that about one third of patients receiving anti-cancer therapy are affected by CIPN, and one third of the patients with CIPN have a permanent neuronal damage (A. Bhagra and R. D. Rao, 2007, Curr Oncol Rep, v9, pp 290-299). The symptoms related to CIPN include numbness in fingers and toes, tingling or burning feeling, cold feeling, pain, and weakened touch sense and muscle strength (T. Armstrong et al., 2005, Oncol Nurs Forum, v32, pp 305-311; C. Visovsky et al., 2008, Clin J Oncol Nurs, v12, pp 243-247).

Anti-cancer agents which are known to cause CIPN include platinum-based anti-cancer agents, taxane-based anti-cancer agents, vinca alkaloids, bortezomib, thalidomide, or the like. The incidence of CIPN is about 20-75% depending on types, dosages, and administration periods of an anti-cancer agents (G. Cavaletti et al., 2011, Curr Treat Options Neurol, v13, pp 180-190). Until now the clear mechanism of neuronal toxicity mediated by an anti-cancer agent has not been elucidated. It has been just presumed that the mechanism underlying cytotoxicity of anti-cancer agents in common cancer cells may be similar to that underlying neuronal toxicity in peripheral nervous system. It is known that the anti-cancer agent administered to a patient is accumulated not only in tumor tissues but also in peripheral nervous system where it exerts neuronal toxicity and induces CIPN.

Until now, there is no standard therapeutic agent available which has been approved by US FDA for CIPN treatment. Anti-seizure agents like gabapentin or anti-depressants like amitriptyline are clinically used to alleviate CIPN-related symptoms. However, large scale clinical studies have failed to prove their efficacy for CIPN treatment. Furthermore, those drugs basically exhibit adverse side effects like dizziness, sleepiness, or the like, and have a disadvantage that administration at high dose is impossible due to their low safety margin. Such medical unmet needs make it urgent to develop a novel safer and more effective therapeutic or preventive agent of CIPN. Because CIPN is considered a complex disease, a multi-target-based drug development may be more appropriate, and thus medicinal plants or natural products which have been traditionally used can be important starting materials from the viewpoint of drug development strategy.

Lithospermi Radix is a root of Boraginaceae including *Lithospermum erythrorhizon* Siebold et Zuccarini, *Arnebia euchroma* Johnst and *Arnebia guttata* Bunge. It has a thin and spindle-like shape with irregular branches, and the length is 6 to 10 cm and the diameter is 5 to 15 mm. The outer surface of Lithospermi Radix has dark purple to purplish brown color, and the skin is rough and easily removable. There are usually twisted vertical grooves, which sometimes reach the neck part. On top of the root, stem hairs are sometimes present. Lithospermi Radix is easily broken, and the cross-section of broken root shows granular shape with many voids. When observed under a magnifier, the horizontal cross-section shows dark purple color on outer skin and the soft brown part inside the cross-section is randomly present. The neck part has yellowish color, and the center of the top part sometimes has voids of which periphery exhibits reddish purple color. Lithospermi Radix has unique mild smell and tastes rather sweet. It is used as a purple dye and known to have effects of lowering body heat, clarifying blood, and improving blood circulation. In Korean Patent Registration No. 0558159, a method to produce health supplement using Lithospermi Radix is disclosed which has an excellent effect on recovery of fatigue and growth of children. Furthermore, in Korean Patent Application Publication No. 2015-0047173, a composition comprising a Lithospermi Radix extract as an effective component is disclosed which is used for preventing or alleviating invasive inflammation in lungs caused by metastasis of acute pancreatitis. However, a technique related to use of Lithospermi Radix for peripheral neuropathy has not been reported yet.

SUMMARY

The inventors of the present invention made an effort to solve the problems described above. As a result, it was found that the Lithospermi Radix extract can relieve the suppressed growth of neurites caused by an anti-cancer agent while neither inducing any cytotoxicity in normal cells nor changing the unique cytotoxic potential of an anti-cancer agent in human cancer cell lines when treated in combination with an anti-cancer agent. In addition, the Lithospermi Radix extract can efficiently lower the increased sensitivity to painful stimuli in peripheral neuropathic animals induced by an anti-cancer agent. The present invention is completed accordingly.

To achieve the purpose described above, the present invention provides a pharmaceutical composition for preventing or treating peripheral neuropathy comprising a Lithospermi Radix extract as an effective component.

The present invention further provides a functional health food composition for preventing or alleviating peripheral neuropathy comprising a Lithospermi Radix extract as an effective component.

The present invention still further provides an anti-cancer supplement comprising a Lithospermi Radix extract as an effective component.

The present invention relates to a composition for preventing, alleviating, or treating peripheral neuropathy, in particular, peripheral neuropathy induced by an anti-cancer agent (i.e., chemotherapy-induced peripheral neuropathy), comprising a Lithospermi Radix extract as an effective component. Specifically, the Lithospermi Radix extract can relieve suppressed growth of neurites caused by an anti-cancer agent while neither inducing any cytotoxicity in normal cells and nor affecting the unique cytotoxic potential of an anti-cancer agent in human cancer cell lines. It can also effectively lower the increased sensitivity to painful stimuli in peripheral neuropathic animals induced by an anti-cancer agent. As such, the Lithospermi Radix extract as an effective component of the present invention can be advantageously used for prevention, alleviation, or treatment of peripheral neuropathy induced by an anti-cancer agent.

No NGF: PC-12 cells not treated with nerve growth factor;

NGF: PC-12 cells treated with nerve growth factor (100 ng/ml);

NGF+Oxal: PC-12 cells simultaneously treated with nerve growth factor (100 ng/ml) and oxaliplatin (150 nM);

NGF+Oxal+V: PC-12 cells simultaneously treated with nerve growth factor (100 ng/ml), oxaliplatin (150 nM), and PBS as a negative control; and NGF+Oxal+WLR: PC-12 cells simultaneously treated with nerve growth factor (100 ng/ml), oxaliplatin (150 nM), and a Lithospermi Radix extract (100 μg/ml).

Figure 3A:
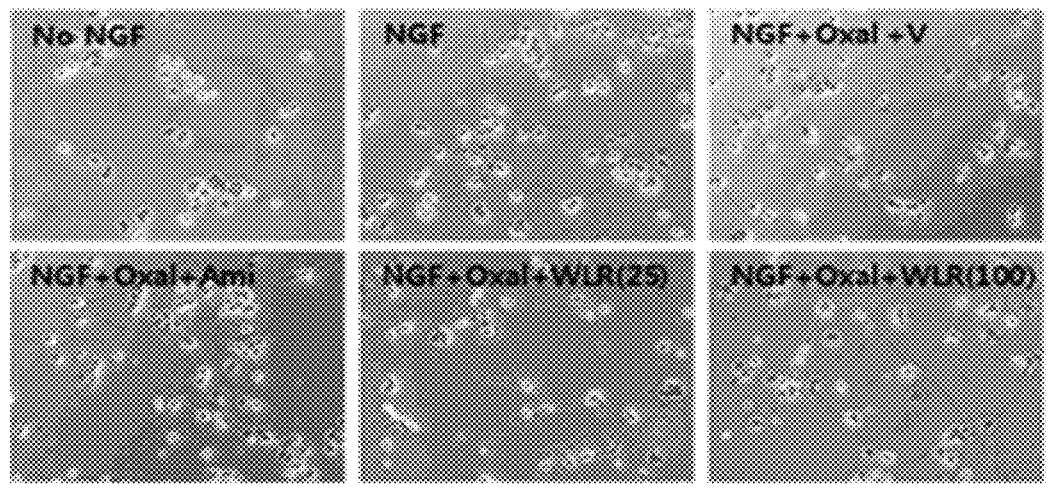
Figure 3B:
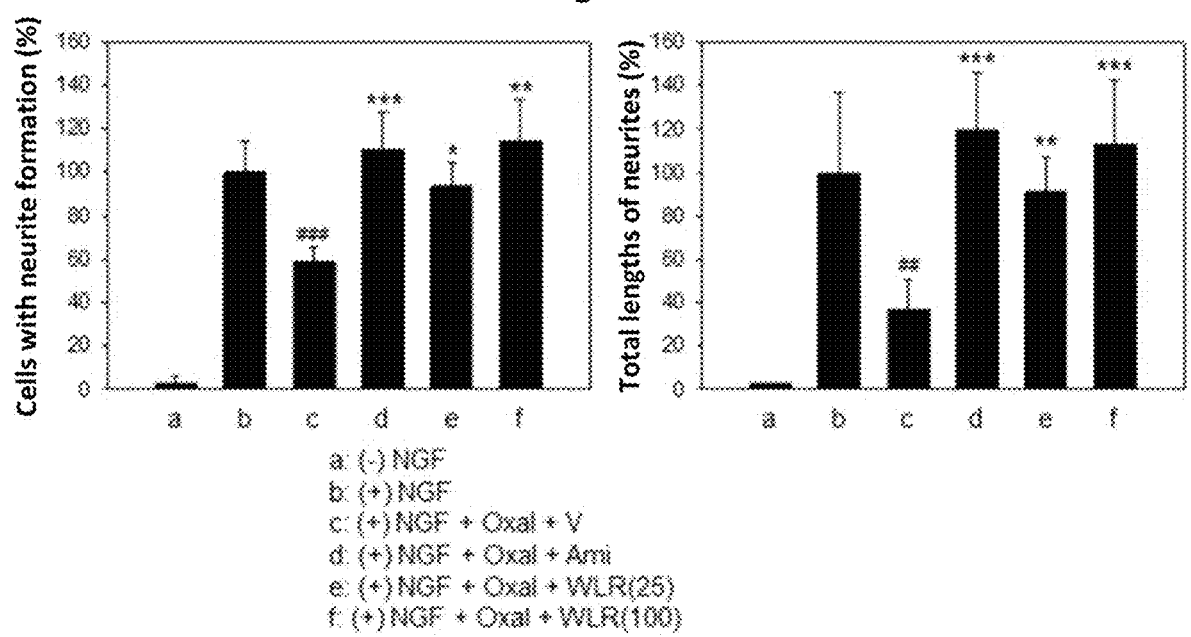

FIG. 3A shows the effect of increasing concentrations of the Lithospermi Radix extract (WLR) of the present invention on neurite growth of PC-12 cells induced by nerve growth factor, and FIG. 3B shows the relative ratios of cells forming neurites and total lengths of growing neurites.

No NGF: PC-12 cells not treated with nerve growth factor;

NGF: PC-12 cells treated with nerve growth factor (100 ng/ml);

NGF+Oxal+V: PC-12 cells simultaneously treated with nerve growth factor (100 ng/ml), oxaliplatin (200 nM), and PBS as a negative control;

NGF+Oxal+Ami: PC-12 cells simultaneously treated with nerve growth factor (100 ng/ml), oxaliplatin (200 nM), and amifostine (4 μg/ml) as a positive control;

NGF+Oxal+WLR (25): PC-12 cells simultaneously treated with nerve growth factor (100 ng/ml), oxaliplatin (200 nM), and a Lithospermi Radix extract (25 μg/ml); and NGF+Oxal+WLR (100): PC-12 cells simultaneously treated with nerve growth factor (100 ng/ml), oxaliplatin (200 nM), and a Lithospermi Radix extract (100 μg/ml), in which ## or ### means that there is a significant difference in means when compared to (+)NGF treatment group (b) (##, $p<0.01$; ###, $p<0.001$), and *, , or * means that there is a significant difference in means when compared to NGF+Oxal+V treatment group (c) (*, $p<0.05$; , $p<0.01$; *, $p<0.001$).

FIG. 4 shows the effect of a Lithospermi Radix extract (WLR) to alleviate peripheral neuropathic pain induced by oxaliplatin in an animal model.

Ctrl: normal control group;

Oxal+V: co-administration of oxaliplatin (10 mg/kg) and 0.5% carboxymethyl cellulose (CMC) as a negative control;

Oxal+WLR: co-administration of oxaliplatin (10 mg/kg) and a Lithospermi Radix extract (250 mg/kg); and Oxal+Ami: co-administration of oxaliplatin (10 mg/kg) and amifostine (100 mg/kg) as a positive control, in which ### means that there is a significant difference in means when compared to the normal control group (Ctrl) ($p<0.001$), and *, , or * means that there is a significant difference in means when compared to a model group (Oxal+V) administered with oxaliplatin (10 mg/kg) and 0.5% CMC as a negative control (*, $p<0.05$; , $p<0.01$; *, $p<0.001$).

Figure 5:
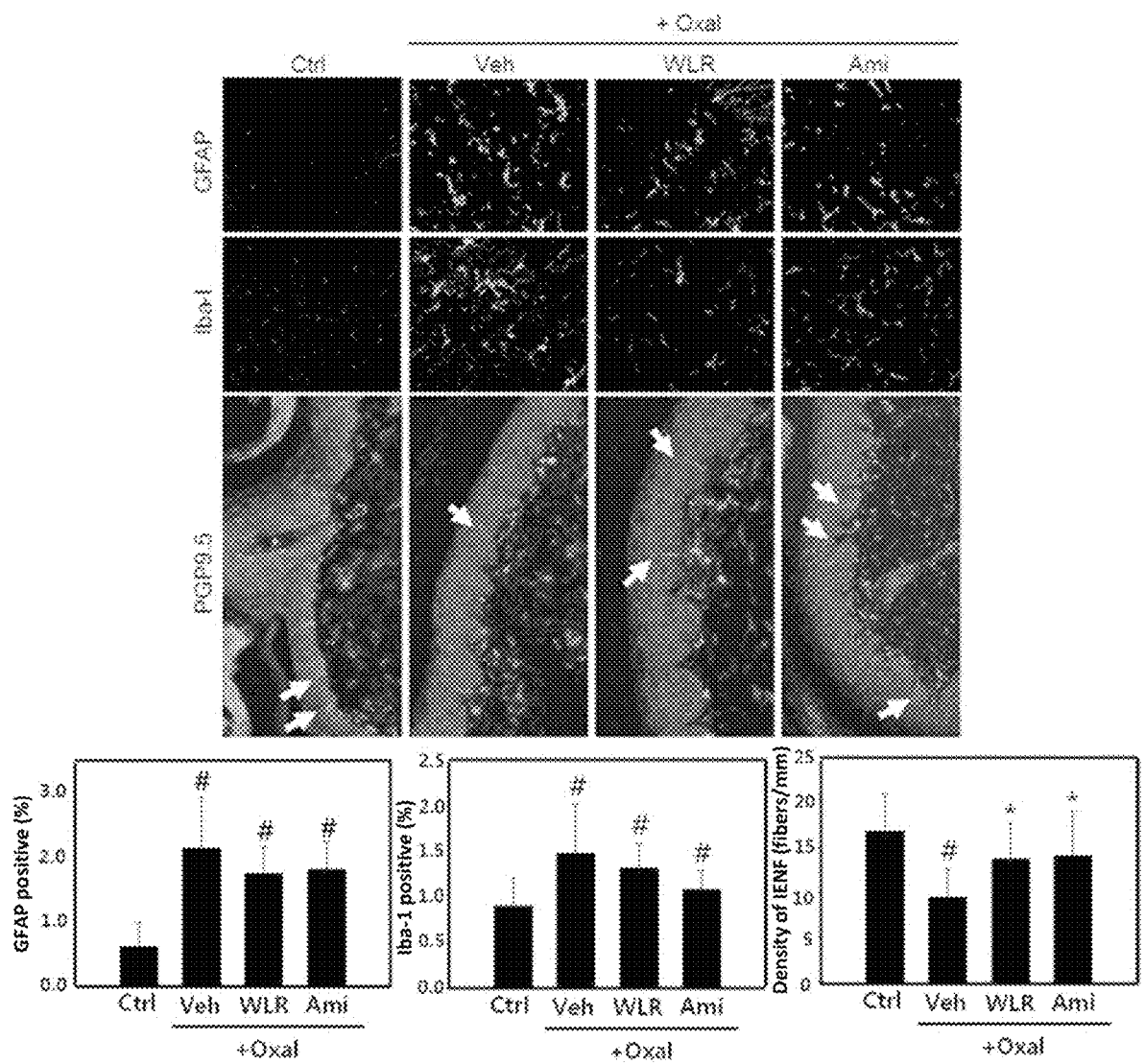

FIG. 5 shows that the Lithospermi Radix extract (WLR) of the present invention can reduce inflammation and neuronal damages in nervous systems induced by oxaliplatin, which was determined by observing the distribution of GFAP and Iba-I in a spinal cord as markers for astrocytes and microglial cells, and PGP9.5 as a marker for intraepidermal nerve fiber (IENF) in the hind footpad of a peripheral neuropathic animals induced by oxaliplatin.

Ctrl: normal control group;

Oxal+Veh: co-administration of oxaliplatin (10 mg/kg) and 0.5% carboxymethyl cellulose (CMC) as a negative control;

Oxal+WLR: co-administration of oxaliplatin (10 mg/kg) and a Lithospermi Radix extract (250 mg/kg); and Oxal+Ami: co-administration of oxaliplatin (10 mg/kg) and amifostine (100 mg/kg) as a positive control, in which # means that there is a significant difference in means when compared to the normal control group (Ctrl) ($p<0.05$), and * means that there is a significant difference in means when compared to a model group (Oxal+Veh) administered with oxaliplatin (10 mg/kg) and 0.5% CMC as a negative control ($p<0.05$).

FIG. 6 shows that the Lithospermi Radix extract (WLR) of the present invention can alleviate the neuronal damages in dorsal root ganglion (DRG) induced by oxaliplatin, which was determined by observing the morphological change of nuclei of DRG neurons in peripheral neuropathic animals induced by oxaliplatin.

Ctrl: normal control group;

Oxal+Veh: co-administration of oxaliplatin (10 mg/kg) and 0.5% carboxymethyl cellulose (CMC) as a negative control;

Oxal+WLR: co-administration of oxaliplatin (10 mg/kg) and a Lithospermi Radix extract (250 mg/kg); and Oxal+Ami: co-administration of oxaliplatin (10 mg/kg) and amifostine (100 mg/kg) as a positive control, in which # means that there is a significant difference in means when compared to the normal control group (Ctrl) ($p<0.05$), and * means that there is a significant difference in means when compared to a model group (Oxal+Veh) administered with oxaliplatin (10 mg/kg) and 0.5% CMC as a negative control ($p<0.05$).

Figure 7:
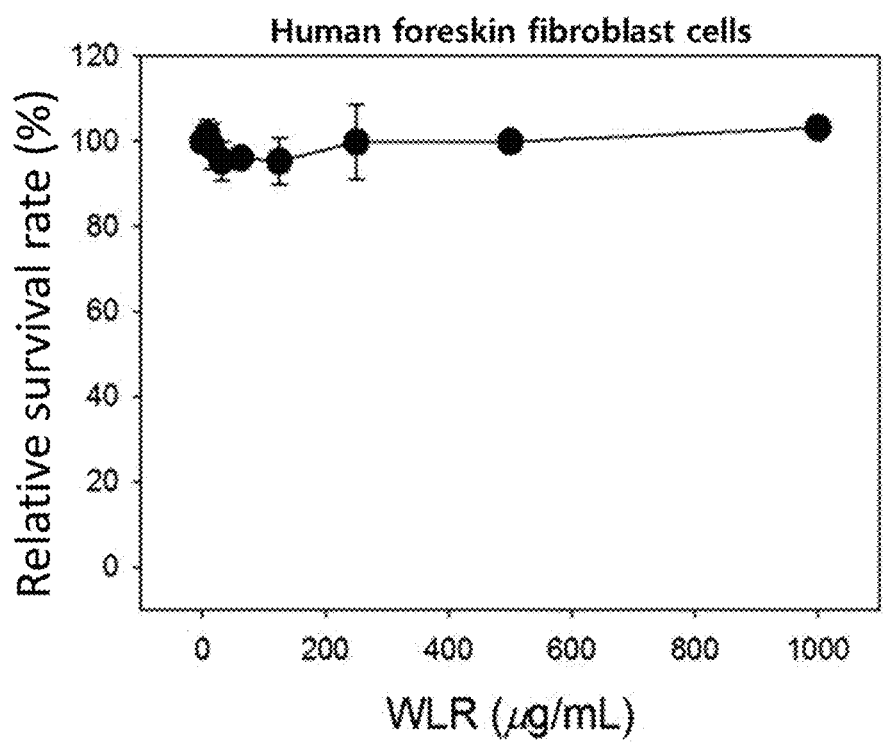

FIG. 7 shows that the Lithospermi Radix extract (WLR) of the present invention is not toxic to normal cells, which was confirmed by measuring the cell survival rate in human foreskin fibroblast cells.

WLR: treatment with a Lithospermi Radix extract (0 to 1000 μg/ml).

Figure 8:
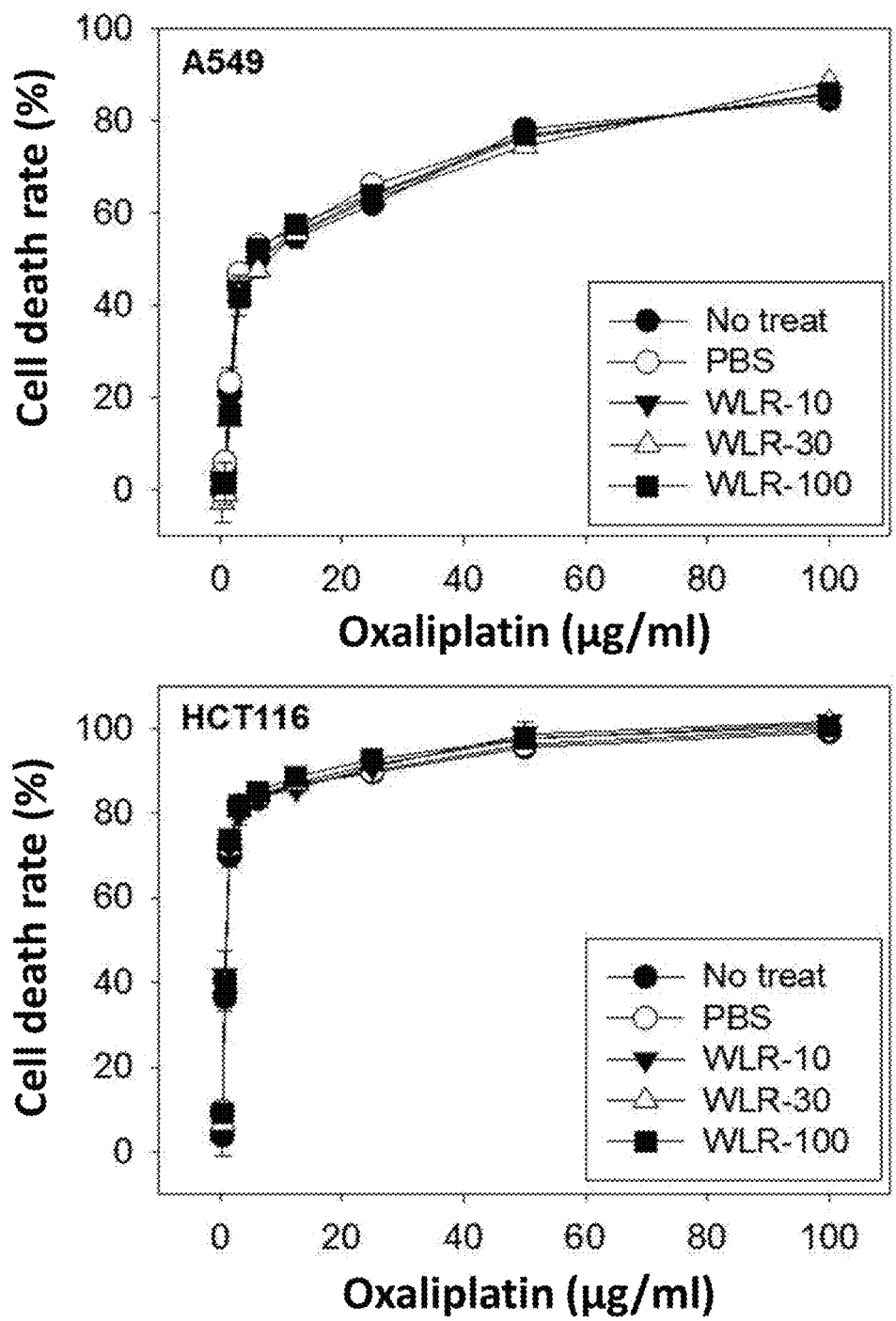

FIG. 8 shows that the Lithospermi Radix extract (WLR) of the present invention does not affect cytotoxic potential of oxaliplatin in cancer cells, when human lung (A549) and colon (HCT116) cancer cells were simultaneously treated with oxaliplatin and the Lithospermi Radix extract of the present invention.

No treat: Treatment only with oxaliplatin (0 to 100 μg/ml);

PBS: Co-treatment with oxaliplatin (0 to 100 μg/ml) and PBS as a negative control;

WLR-10: Co-treatment with oxaliplatin (0 to 100 μg/ml) and a Lithospermi Radix extract (10 μg/ml);

WLR-30: Co-treatment with oxaliplatin (0 to 100 μg/ml) and a Lithospermi Radix extract (30 μg/ml); and WLR-100: Co-treatment with oxaliplatin (0 to 100 μg/ml) and a Lithospermi Radix extract (100 μg/ml).

Figure 9A:
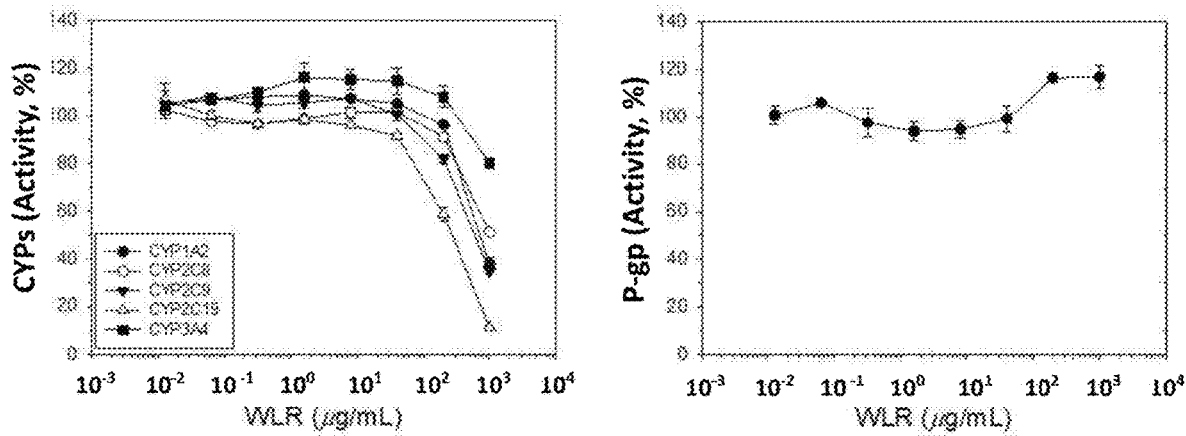
Figure 9B:
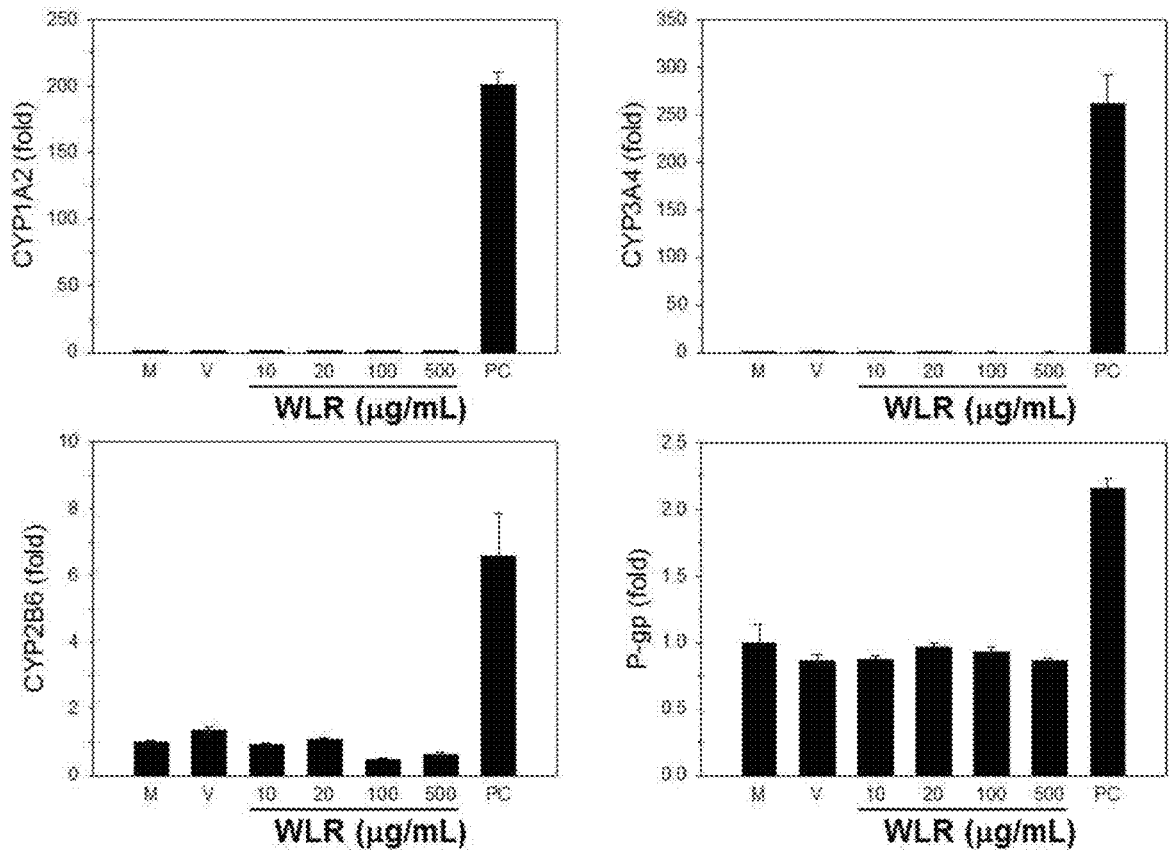

FIG. 9A shows the inhibitory effect of the Lithospermi Radix extract (WLR) of the present invention on the activity of CYP human drug metabolism enzyme and P-gp drug transporter, which was biochemically determined. FIG. 9B shows the effect of the Lithospermi Radix extract (WLR) of the present invention on induction of CYP and P-gp gene expression in HepaRG human hepatoma cell line, which was determined by in vitro tests and real-time polymerase chain reactions (PCR).

M: Normal HepaRG cells;

V: HepaRG cells treated with PBS as a negative control;

WLR: HepaRG cells treated with a Lithospermi Radix extract (10, 20, 100, 500 μg/ml); and PC: HepaRG cells treated with, 50 μM omeprazole for CYP1A2 and CYP2B6, or with 10 μM rifampicin for CYP3A4 and P-gp as a positive control.

DETAILED DESCRIPTION

The present invention provides a pharmaceutical composition for preventing or treating peripheral neuropathy comprising a Lithospermi Radix extract as an effective component.

The extract is preferably obtained by extraction using water, lower alcohol of $C_1$ to $C_4$, or a mixture thereof as a solvent, and the lower alcohol is preferably ethanol or methanol.

The Lithospermi Radix extract is preferably produced by a production method comprising the followings, but it is not limited thereto:

1) carrying out extraction by adding an extraction solvent to Lithospermi Radix;
2) filtering an extract of above step 1); and
3) concentrating the extract under reduced pressure which is obtained by filtering in above step 2) followed by drying.

With regard to the above method, the Lithospermi Radix of the step 1) can be used without any limitation, i.e., any one of cultivated Lithospermi Radix and commercially available Lithospermi Radix can be used.

With regard to the above method, a method commonly used in the pertinent art like a filtration method, a hot water extraction, an impregnation extraction, a reflux cooling extraction, and ultrasonic extraction can be used as a method for extracting Lithospermi Radix of the step 1). It is preferable that the extraction is made by adding an extraction solvent to a volume of 2 to 40 times as much dried Lithospermi Radix. The extraction temperature is preferably 20 to 100° C., but not limited thereto. Furthermore, the extraction time is preferably 0.5 to 10 hours. Specifically, it is more preferably 1 to 4 hours, and most preferably 2 hours, but not limited thereto. Furthermore, the extraction is preferably repeated 2 times, but not limited thereto.

With regard to the method described above, a vacuum evaporator or a vacuum rotary evaporator is preferably used for concentration under reduced pressure of the step 3), but it is not limited thereto. Furthermore, the drying is preferably carried out by drying under reduced pressure, vacuum drying, drying with boiling, spray drying, or freeze drying, but it is not limited thereto.

The peripheral neuropathy is preferably induced by an anti-cancer agent, and examples of the anti-cancer agent include platinum-based anti-cancer agents, taxane-based anti-cancer agents, vinca alkaloids, bortezomib, and thalidomide, but not limited thereto, and all anti-cancer agents that can be clinically, pharmaceutically, or biomedically used are included therein.

The platinum-based anti-cancer agents are preferably at least one selected from a group consisting of cisplatin, carboplatin, and oxaliplatin, but it is not limited thereto. The taxane-based anti-cancer agents are preferably at least one selected from a group consisting of paclitaxel and docetaxel, but it is not limited thereto.

The pharmaceutical composition of the present invention may have various kinds of formulations like oral formulation and parenteral formulation, and it is prepared by using a diluent or a vehicle like a filling agent, a bulking agent, a binding agent, a wetting agent, a disintegrating agent, and a surface active agent that are commonly used for formulating a composition.

Examples of a solid preparation for oral administration include a tablet, a pill, a powder, a granule, and a capsule, and the solid preparation is prepared by mixing at least one compound with at least one vehicle such as starch, calcium carbonate, sucrose, lactose, or gelatin. Furthermore, other than simple vehicles, a lubricating agent such as magnesium stearate or talc is also used. Examples of a liquid preparation for oral administration include a suspension, a solution for internal use, an emulsion, and a syrup, and also various kinds of a vehicle like a wetting agent, a sweetening agent, an aroma, and a preservative may be included in addition to water and liquid paraffin that are generally used as a simple diluents.

A preparation for parenteral administration includes a sterilized aqueous solution, a non-aqueous preparation, a suspension preparation, an emulsion, a freeze-dry preparation, and a suppository. For the non-aqueous preparation and suspension preparation, propylene glycol, polyethylene glycol, plant oil like olive oil, and injectable ester like ethylolate can be used. As a base of a suppository, witepsol, macrogol, tween 61, cacao fat, laurin fat, glycerol, gelatin, or the like can be used.

The pharmaceutical composition of the present invention can be administered either orally or parenterally, and in case of parenteral administration, external application to skin, or intraperitoneal, rectal, intravenous, intramuscular, subcutaneous, uterine intrathecal, or intra-cerebrovascular injection can be preferably selected, but it is not limited thereto.

The pharmaceutical composition of the present invention is administered in a pharmaceutically effective amount. In the present invention, the pharmaceutically effective amount means an amount which is sufficient for treating a disorder at benefit/risk ratio that can be applied to a medical treatment, and the level of effective dosage can be determined based on elements including type or severity of a disorder of a patient, activity of a pharmaceutical, sensitivity to a pharmaceutical, administration time, administration route, discharge ratio, period for treatment, drugs that are simultaneously used, and other elements that are well known in the medical field. The composition of the present invention can be administered either as an independent therapeutic agent or in combination with other therapeutic agent. It can be administered either sequentially or simultaneously with a conventional therapeutic agent, and also can be administered once or several times. It is important to have administration in an amount which allows obtainment of the maximum effect with a minimum amount without having any adverse side effect while all factors described above are taken into consideration, and the amount can be easily determined by a person skilled in the art.

Dosage of the composition of the present invention varies widely depending on body weight, age, sex, health state, and diet of a patient, administration time, administration method, excretion rate, and severity of a disorder. The daily dosage is, in terms of the amount of Lithospermi Radix extract, 0.01 to 1000 mg/kg, preferably 30 to 500 mg/kg, and more preferably 50 to 300 mg/kg, and it can be administered 1 to 6 times per day. However, as it can be increased or decreased depending on administration route, severity of obesity, sex, body weight, age, or the like, the scope of the present invention is not limited in any sense by the dosage described above.

The pharmaceutical composition of the present invention is preferably used in combination with an anti-cancer agent, but it can be also used either singly or in combination with surgical operation, radiation therapy, hormone therapy, or a method of using biological response regulator.

The present invention further provides a functional health food composition for preventing or alleviating peripheral neuropathy comprising a Lithospermi Radix extract as an effective component.

The extract is preferably obtained by extraction using water, lower alcohol of $C_1$ to $C_4$, or a mixture thereof as a solvent, and the lower alcohol is preferably ethanol or methanol.

The Lithospermi Radix extract is preferably produced by a production method comprising the followings, but it is not limited thereto:
1) carrying out extraction by adding an extraction solvent to Lithospermi Radix;
2) filtering an extract of above step 1); and
3) concentrating the extract under reduced pressure obtained by filtering in above step 2) followed by drying.

With regard to the above method, the Lithospermi Radix of the step 1) can be used without any limitation, i.e., any one of cultivated Lithospermi Radix and commercially available Lithospermi Radix can be used.

With regard to the above method, a method commonly used in the pertinent art like a filtration method, a hot water extraction, an impregnation extraction, a reflux cooling extraction, and ultrasonic extraction can be used as a method for extracting Lithospermi Radix of the step 1). It is preferable that an extraction is made by adding an extraction solvent to a volume of 2 to 40 times as much the amount of dried Lithospermi Radix. The extraction temperature is preferably 20 to 100° C., but not limited thereto. Furthermore, the extraction time is preferably 0.5 to 10 hours. Specifically, it is more preferably 1 to 4 hours, and most preferably 2 hours, but not limited thereto. Furthermore, the extraction is preferably repeated 2 times, but not limited thereto.

With regard to the method described above, a vacuum evaporator or a vacuum rotary evaporator is preferably used for the concentration under reduced pressure of the step 3), but it is not limited thereto. Furthermore, the drying is preferably carried out by drying under reduced pressure, vacuum drying, drying with boiling, spray drying, or freeze drying, but it is not limited thereto.

The peripheral neuropathy is preferably induced by an anti-cancer agent, and examples of the anti-cancer agent include platinum-based anti-cancer agents, taxane-based anti-cancer agents, vinca alkaloids, bortezomib, and thalidomide, but not limited thereto, and all anti-cancer agents that can be clinically, pharmaceutically, or biomedically used are included therein.

The platinum-based anti-cancer agents are preferably at least one selected from a group consisting of cisplatin, carboplatin, and oxaliplatin, but it is not limited thereto.

The taxane-based anti-cancer agents are preferably at least one selected from a group consisting of paclitaxel and docetaxel, but it is not limited thereto.

The functional health food product can be produced and processed in the form of a tablet, a capsule, a powder, a granule, a liquid, a pill or the like, but it is not limited thereto and it can be produced and processed in any form according to the regulations.

The composition comprising the Lithospermi Radix extract of the present invention as an effective component can be directly added to a food, or used with other food or food components, and it can be suitably used according to a common method. The mixing amount of an effective component can be suitably determined depending on the purpose of use (i.e., for prevention or alleviation). In general, the amount of the extract in a health food product can be 0.1 to 90 parts by weight relative to the total weight of a food product. However, when it is used for a long period of time under the purpose of health and hygiene or health management, the addition amount can be lower than the amount of the above range, and as it has no problem in terms of safety, the effective component can be also used in an amount which is more than the amount of the above range.

With regard to the functional health drink composition of the present invention, other components are not particularly limited except that the above extract is contained as an essential component at the indicated ratio. Like a common drink, various kinds of flavors, natural carbohydrates, or the like, can be contained as an additional component. Examples of the natural carbohydrate include common sugars like monosaccharides such as glucose or fructose; disaccharides such as maltose or sucrose; and polysaccharides such as dextrin or cyclodextrin, and sugar alcohols such as xylitol, sorbitol, or erythritol. As a flavor other than those described above, a natural flavor (thaumatin, *stevia* extract (for example, rebaudioside A, glycyrrhizin, or the like)), and a synthetic flavor (saccharine, aspartame, or the like) can be advantageously used.

Other than those described above, the Lithospermi Radix extract of the present invention may contain various kinds of nutritional agent, vitamins, minerals (electrolytes), flavors like synthetic flavors and natural flavors, a coloring agent, an enhancing agent (cheese, chocolate, or the like), pectinic acid and a salt thereof, alginic acid and a salt thereof, organic acids, a protective colloid thickening agent, a pH controlling agent, a stabilizer, a preservative, glycerin, alcohols, and a carbonating agent used for soda drink. In addition, the Lithospermi Radix extract of the present invention may contain fruit flesh for producing natural fruit juice, fruit juice drink, or vegetable drink. Those components may be used either independently or in combination thereof. The mixing ratio of those additives is not critical, but it is generally selected within a range of 0.1 to about 20 parts by weight per 100 parts by weight of the Lithospermi Radix extract of the present invention.

The present invention still further relates to an anti-cancer supplement comprising a Lithospermi Radix extract as an effective component. The extract is as described above.

The anti-cancer supplement is preferably administered in combination with an anti-cancer agent including platinum-based anti-cancer agents, taxane-based anti-cancer agents, vinca alkaloids, bortezomib, and thalidomide, and the anti-cancer supplement preferably has an effect of preventing or treating peripheral neuropathy that is induced by an anti-cancer agent.

Hereinbelow, the present invention is explained in greater detail in view of the Examples. However, it would be evident to a person who has common knowledge in the pertinent art that the following Examples are given only for further specific explanation of the present invention and by no means the present invention is limited to the following Examples.

[Materials and Methods]

1. Preparation of the Lithospermi Radix Extract (WLR)

One hundred grams of dry Lithospermi Radix purchased from Kwangmyungdang Pharmaceuticals (Ulsan, South Korea) were ground to prepare a sample in a powder form. One hundred grams of the ground dry sample and 2 liters of water were added to a round flask and mixed therein. Extraction was carried out by heating it in a water bath which was connected to a reflux extraction device equipped with a condenser, total 2 times, 2 hours per each extraction. The obtained extract was filtered under reduced pressure by using a filter paper (Whatman No. 2) and a vacuum pump (GAST). The filtered liquid extract was concentrated under reduced pressure using a rotary evaporator (EYELA). The concentrated extract was subjected to freeze-drying, homogenized using a mortar and pestle, and finally, a water extract of Lithospermi Radix (i.e., WLR) was obtained. The water extract of Lithospermi Radix was placed in a tight-fitting plastic container and stored at 4° C. until it was used for the test.

2. High Performance Liquid Chromatography (HPLC) Analysis of Lithospermi Radix Extract (WLR)

In order to identify the components contained in the Lithospermi Radix extract (WLR) obtained according to [Materials and Methods 1], a high performance liquid chromatography (HPLC) was carried out under the following conditions. Specifically, 40 mg of the Lithospermi Radix extract (WLR) was dissolved in 1 ml of distilled water followed by filtering. For HPLC analysis, the sample was injected in an amount of 20 μl. As for the mobile phase solvent A, 0.1% (v/v) trifluoroacetic acid (TFA, Samchun Pure Chemical Co., Ltd) in ultrapure water (Honeywell Brudic-Jackson) was used. As for the solvent B, acetonitrile (J. T Baker, Avantor Performance Material, Inc.) was used. For HPLC analysis, Waters Alliance e2695 (Waters Corporation) equipped with e2695 separation module and 2998 photodiode array detector was used. The Phenomenmex Luna C18 (2) (250×4.6 mm, 5 μm) column was used for separation. Column temperature was set at 40° C. and detector wavelength was set at 254 nm. The separation was carried out by applying a gradient between the solvent A and the solvent B for 60 minutes in total with concentration gradients as follows: 0 to 10 minutes, ratio (v/v) of the solvent B:the solvent A=90%:10%, 10 to 60 minutes, ratio (v/v) of the solvent B:the solvent A=90%:10% to 40%:60%. The substances contained in the Lithospermi Radix extract were identified by comparing the retention times (RT) and the UV spectra of the Lithospermi Radix extract and reference standards under the same analytical conditions.

3. Cell Culture 3-1. PC-12 Cell Culture

PC-12 was purchased from the ATCC (USA). The cells were cultured in a 100 mm cell culture dish coated with collagen type I in an incubator at 37° C., 5% $CO_2$, using a DMEM basal medium supplemented with 5% non-heat inactivated fetal bovine serum (FBS), 10% heat inactivated horse serum (HS), 100 unit/ml penicillin, and 100 μg/ml streptomycin. The basal medium, sera, and other additives were purchased from the Thermo Fisher Scientific.

3-2. Human Foreskin Fibroblast Cell Culture

Human foreskin fibroblast cell was purchased from System Biosciences. The human foreskin fibroblast cells were cultured in a 100 mm cell culture dish in an incubator at 37° C., 5% $CO_2$, using a DMEM basal medium supplemented with 10% heat inactivated FBS, 100 unit/ml penicillin, and 100 μg/ml streptomycin, and then used for in vitro tests. The basal medium, serum, and other additives were purchased from the Thermo Fisher Scientific.

3-3. Culture of Human Lung Cancer Cell (A549) and Human Colon Cancer Cell (HCT116)

A549 and HCT116 cells were purchased from the ATCC (USA). They were cultured in a 100 mm cell culture dish in an incubator at 37° C., 5% $CO_2$, using an RPMI1640 basal medium supplemented with 10% heat inactivated FBS, 100 unit/ml penicillin, and 100 μg/ml streptomycin, and then used for in vitro tests. The basal medium, serum, and other additives were purchased from the Thermo Fisher Scientific.

3-4. Human Hepatoma Cell Line (HepaRG) Culture

HepaRG was purchased from the Thermo Fisher Scientific. The cells were used immediately after purchase without any subculture. A William's medium E basal medium supplemented with Thaw, Plate & General Purpose Supplements was used for general cell culture. A William's medium E basal medium supplemented containing Induction Medium Supplements was used for induction experiment. The cells were cultured in a 24-well culture plate coated with collagen type I in an incubator at 37° C., 5% $CO_2$. All culture media and additives used for HepaRG cell culture were purchased from the Thermo Fisher Scientific.

4. Peripheral Neuropathic Animal Model Induced by Anti-Cancer Agent (Chemotherapy-Induced Peripheral Neuropathy, CIPN)

In the present invention, an animal model having peripheral neuropathy was induced by oxaliplatin. Eight-week old male C57BL/6 mice were purchased from the OrientBio. Following 1 week acclimation period in a cage in an animal test room, the base line (BL) of responses of experimental animals to 3 times of mechanical stimulations applied to the right hind footpad of the animal using von Frey filament hair. Then, the animals were divided into different groups (N=8 animals/group). Peripheral neuropathy was induced by injection of 5 mg/kg oxaliplatin through tail veins of animals (once a week, 2 times for 2 weeks, i.e., 10 mg/kg oxaliplatin in total). Oxaliplatin was purchased from the LC Laboratories.

5. Measurement of Mechanical Allodynia

The mouse with peripheral neuropathy, which was induced by oxaliplatin for 2 weeks, was acclimated for 1 hour in a cage with wire grids manufactured by the UGO BASILE. Then, the frequency (%) of the animals was determined which showed a response of retracting the paw when applying a stimulus of 0.4 g with von Frey filament hair to the right hind footpad.

6. Histological Analysis Using Specimens of Test Animals 6-1. Preparation of Specimens The specimens were prepared to histologically determine the protective effect of the Lithospermi Radix extract (WLR) against neuronal damage in peripheral neuropathic animals induced by oxaliplatin. Specifically, the animal was anaesthetized by intraperitoneal injection of sodium pentobarbital (50 mg/kg), and then, blood was removed by perfusion of 0.9% physiological saline through the aorta via left ventricle. Following fixation by perfusion of 4% paraformaldehyde solution buffered with 0.1 M phosphate, the $4^{th}$ to $6^{th}$ lumbar spinal cords, dorsal root ganglia, and the hind footpad skins were removed. The tissues were further fixed in the same fixation solution as above. The paraffin-embedded tissues were sectioned at a 4 µm thickness. The slices were mounted on a glass slide, dried, and then, kept at room temperature until use.

6-2. Immunohistological Analysis of Glial Cells

The slice of spinal cord with 4 µm thickness was subjected to immunofluorescence staining using antibodies against GFAP and Iba-1 which are astrocyte and microglial cell markers, respectively. After removal of paraffin and hydration, the slice was immersed in citrate buffer solution (Vector Lab., USA) for 10 minutes in a microwave to recover antigenicity and increase reactivity.

All reactions were carried out in Tris buffer solution containing 0.05% Tween 20 (i.e., TBS-T) to increase permeability and to prevent loss of thin slice. The tissue slice was blocked for 1 hour in TBS-T solution containing 10% normal goat serum (NGS) to prevent a non-specific antigen-antibody binding, and then, incubated for 24 hours at 4° C. in GFAP or Iba-1 antibody solution which was diluted at 1:200. After washing 3 times with TBS-T, the slice was incubated for 1 hour at room temperature in a secondary antibody solution labeled with a fluorescent dye which was diluted at 1:2000. After washing 3 times with TBS-T again, the slice was covered with a cover glass to prevent loss of the specimen.

The activity of the glial cells was expressed by the ratio (%) of the area of stained cells relative to the viewing area under a fluorescence microscope. The fluorescence microscopic images were analyzed compared to the control treatment using a software (Cellsense, Olympus).

6-3. Quantitative Histological Analysis of Intraepidermal Nerve Fiber (IENF)

The slice of hind footpad skin with 4 µm thickness was subjected to immunofluorescence staining using a PGP9.5 antibody, a marker for IENF in skin. After removal of paraffin and hydration, the slice was immersed in a citrate buffer solution (Vector Lab., USA) for 10 minutes in a microwave to recovery antigenicity and increase reactivity. All reactions were carried out in a Tris buffer solution containing 0.05% Tween 20 (i.e., TBS-T) to increase permeability and prevent loss of the thin slice. The slice was blocked for 1 hour in the TBS-T solution containing 10% normal goat serum (NGS) to prevent a non-specific antigen-antibody binding, and incubated in a PGP9.5 antibody solution for 24 hours at 4° C. which was diluted at 1:200. After washing 3 times with TBS-T, the slice was incubated for 1 hour at room temperature in a secondary antibody solution labeled with a fluorescent dye which was diluted at 1:2000. After washing 3 times with TBS-T, the slice was covered with a cover glass to prevent loss of the specimen. The expression level of intraepidermal nerve fibers was expressed by the number of fluorescence-stained nerves in epidermis which were stemmed from dermis per field length of the basal membrane of epidermis (IENF/mm) within a viewing area under a fluorescence microscope. The fluorescent microscopic images were analyzed compared with control treatment using a software (Cellsense, Olympus).

6-4. Morphological Cell Analysis of Dorsal Root Ganglion

Dorsal root ganglions were cut out, sectioned into slices with 4 µm thickness and then, subjected to Azan-Mallory trichrome staining. The nucleoli in the stained slice were examined under an optical microscope. Among the neurons having discernible nucleoli, the number of neurons having eccentric nucleoli or multinucleolated nucleus was expressed as a percentage of the total neurons in a viewing area.

7. Activity Analysis of Human Drug Metabolism Enzyme (CYP) and Drug Transporter (P-Gp)

7-1. In Vitro Enzyme Inhibition

To determine whether the Lithospermi Radix extract (WLR) can inhibit the activity of a human drug metabolism enzyme (CYP) and a drug transporter (P-gp), P450-Glo assay and Pgp-Glo assay were carried out. The systems which use luciferin enzyme were purchased from the Promega or the Thermo Fisher Scientific.

For CYP reaction, 12.5 µl of a reaction mixture containing each enzyme, substrate, and potassium phosphate was added to each well of a 96-well plate. Following addition of the Lithospermi Radix extract at final concentrations of 0 to 1,000 µg/ml, the mixture was pre-incubated at 37° C. for 10 to 40 minutes depending on the types of enzyme. Enzyme reaction was initiated by adding 25 µl NADPH regeneration system. After mixing, the reaction mixture was incubated at 37° C. for 10 to 45 minutes depending on the types of enzyme. The luciferase reaction was initiated by adding 50 µl detection solution and the mixture was incubated for 10 to 30 minutes at room temperature.

For P-gp reaction, 20 µl sodium vanadate was added to each well of a 96-well plate. After that, 10 µl of 1 mM verapamil and the Lithospermi Radix extract (0 to 1000 µg/ml) were added to each well. Following addition of 20 µl diluted P-gp enzyme, the mixture was incubated at 37° C. for 5 minutes. Then, ATP reaction was initiated by adding 10 µl MgATP which corresponds to ⅕ of the final P-gp reaction mixture and the mixture was incubated for 80 minutes at 37° C. Following addition of 50 µl of ATP detection reagent, the mixture was incubated for 20 minutes at room temperature.

The luminescence intensity was measured using a TriStar LB 941 Multimode Microplate Reader (Berthold Technologies) and expressed as relative luminescence units (RLU).

7-2. In Vitro Induction of Enzyme Gene Expression

According to [Materials and Methods 3-4], human hepatoma cell line (HepaRG) were plated at 5×10⁵ cells/ml in a 24-well plate coated with collagen type I and cultured for 72 hours at 37° C., 5% $CO_2$. Then, the cells were treated for 24 hours with a positive control drug or with a Lithospermi Radix extract (WLR) at concentrations of 10, 20, 100, and 500 µg/ml. For a positive control drug, 50 µM omeprazole was used for CYP1A2 and CYP2B6, and 10 µM rifampicin was used for CYP3A4 and P-gp. Distilled water was used as a negative control. After 24 hours, total RNA was extracted using an Easy-Spin™ Total RNA extraction kit (iNtRON Biotechnology). cDNA was synthesized from total RNA (500 ng) using oligo dT and iScript cDNA synthesis kit (Bio-Rad). Real-time PCR was carried out using a synthesized cDNA as a template and SYBR Green (Bio-Rad) by 40 cycles of 95° C. for 5 seconds and 60° C. for 30 seconds in a T100 Thermal Cycler (Bio-Rad). The primers for human drug metabolism enzyme (CYP), drug transporter (P-gp), and GAPDH (glyceraldehyde 3-phosphate dehydrogenase) as a reference control are summarized in Table 1. The mean $C_t$ values of the human drug metabolism enzyme (CYP) and drug transporter (P-gp) were obtained by repeating the tests 3 times, and they were normalized by the $C_t$ value of GAPDH.

TABLE 1

Primers and nucleotide sequences for real-time PCR of human CYP and P-gp

| Target gene | SEQ ID NO: | Primers | Nucleotide sequence (5'→3') |
|---|---|---|---|
| CYP1A2 | 1 | Forward | TGAATGGCTTCTACATCCCC |
| CYP1A2 | 2 | Reverse | AGGGCTTGTTAATGGCAGTG |
| CYP3A4 | 3 | Forward | CCCACACCTCTGCCTTTTT |
| CYP3A4 | 4 | Reverse | GCACAGGCTGTTGACCATC |
| CYP2B6 | 5 | Forward | CCCCAAGGACACAGAAGTATTTC |
| CYP2B6 | 6 | Reverse | GATTGAAGGCGTCTGGTTTTC |
| P-gp | 7 | Forward | GCCAAAGCCAAAATATCAGC |
| P-gp | 8 | Reverse | TTCCAATGTGTTCGGCATTA |
| GAPDH | 9 | Forward | AAGGCTGAGAACGGGAAG |
| GAPDH | 10 | Reverse | GGACTCCACGACGTACTC |

8. Statistical Analysis

The results were expressed as means±standard deviation (mean±S.D.). ANOVA/Bonferroni post-hoc test was carried out for statistical comparison of means among groups. p value was expressed as * or #<0.05,  or ##<0.01, * or ###<0.001.

Example 1. HPLC Analysis of the Lithospermi Radix Extract

Figure 1:
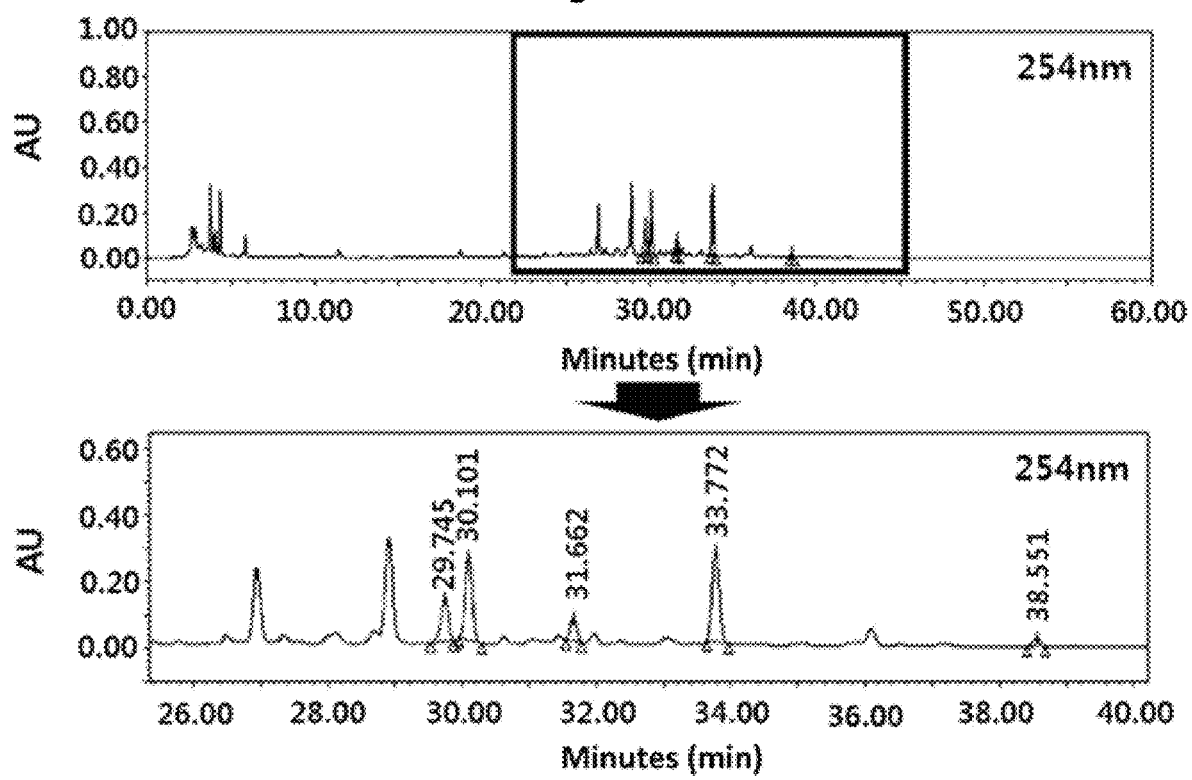
FIG. 1A is a chromatogram to analyze a component profile of the Lithospermi Radix extract (WLR) using a high performance liquid chromatography (HPLC) at a UV detector wavelength of 254 nm.
FIG. 1B is a table summarizing indicator components which have been identified as main peaks in the HPLC chromatogram at a UV detector wavelength of 254 nm when compared with the standards.

The HPLC analysis of the Lithospermi Radix extract (WLR) prepared according to [Materials and Methods 1] was carried out as described in [Materials and Methods 2]. Five peaks were identified when comparing the retention times (RT) and UV spectra of the components contained in the Lithospermi Radix extract (WLR) and the reference standards (FIGS. 1A and 1B). The 5 peaks were identified as follows: rosmarinic acid with RT value of 29.745 minutes, lithospermic acid with RT value of 30.101 minutes, salvianolic acid B with RT value of 31.662 minutes, salvianolic acid A with RT value of 33.772 minutes, and salvianolic acid C with RT value of 38.551 minutes.

Example 2. Determination of the Neuroprotective Effect of the Lithospermi Radix Extract In Vitro 2-1. Neuroprotective Effect of the Lithospermi Radix Extract—Qualitative Analysis The neuroprotective effect of the Lithospermi Radix extract of the present invention was determined using a neurite outgrowth analysis kit (NS225, Millipore) with 1 µm pore-sized membrane.

Specifically, PC-12 was cultured according to [Materials and Methods 3-1] for 72 hours in a DMEM low serum-differentiation medium supplemented with 1% horse serum, 100 unit/ml penicillin, 100 µg/ml streptomycin, and 100 ng/ml nerve growth factor (NGF). The membrane with 1 µm pores was coated by immersing it in a 24-well plate containing a 10 µg/ml collagen solution in an amount of 400 µl/well for 2 hours at 37° C. The collagen-coated membrane was transferred to a well containing a 600 µl of differentiation medium, and then, the differentiated PC-12 cells for 72 hours were plated at 75,000 cells/100 µl/membrane. The cells were treated with 200 nM oxaliplatin to induce neurotoxicity. The cells were co-treated with oxaliplatin and 100 µg/ml Lithospermi Radix extract prepared according to [Materials and Methods 1] to determine its neuroprotective effect on neurite growth. In addition, the cells were co-treated with oxaliplatin and PBS as a negative control. The cells were cultured for 48 hours at 37° C. for neurites to outgrow through the bottom surface of the membrane. After 48 hours, the membrane was removed, washed with PBS, and fixed with methanol for 20 minutes. The membrane was then immersed for 30 minutes in a well containing a 400 µl neurite staining solution. After staining, the top surface of the membrane was cleared with a cotton swab to remove cell bodies. The stained membrane was washed with PBS, and the neurites outgrowing through the bottom surface of the membrane was examined under an optical microscope.

Figure 2:
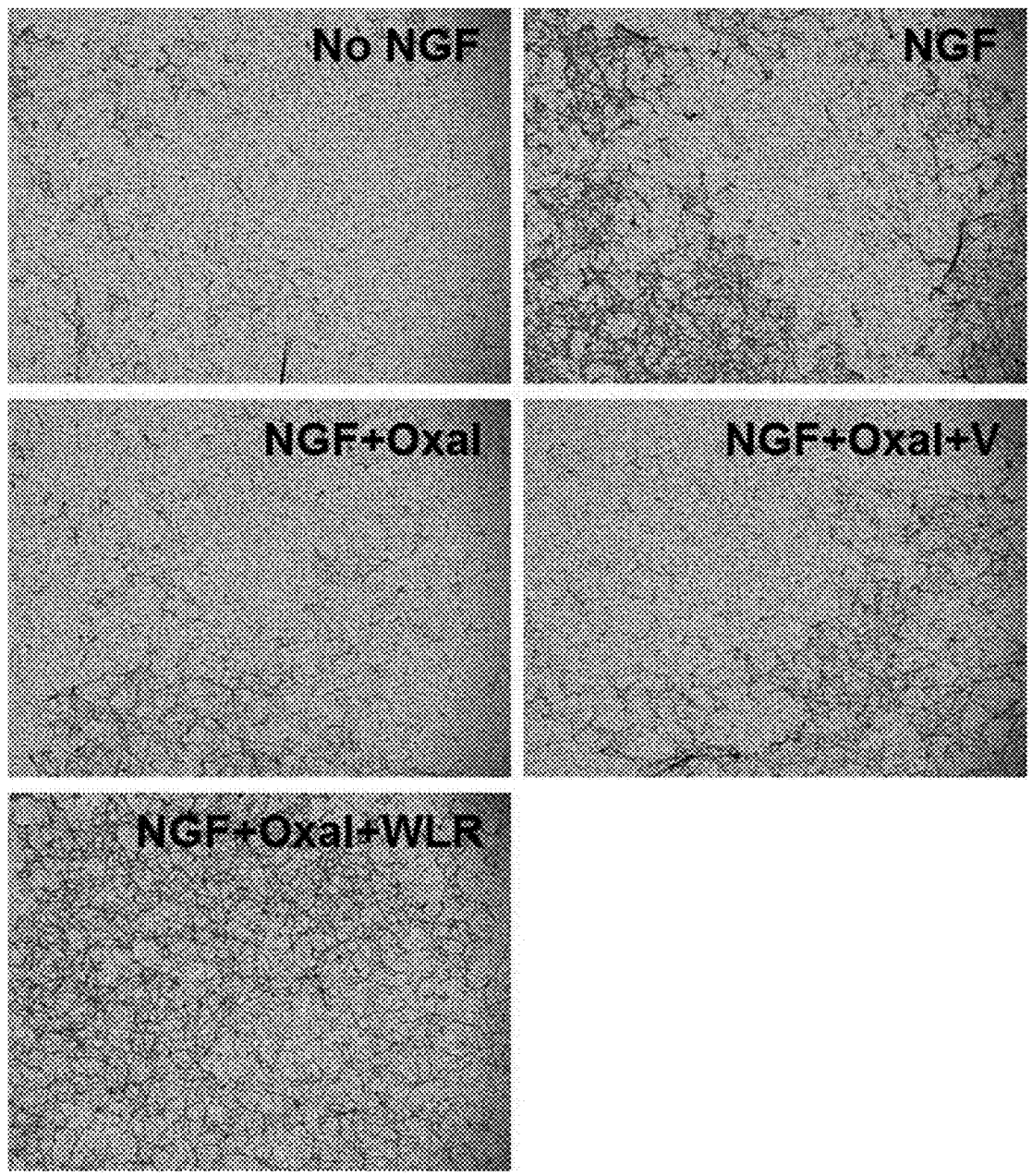
FIG. 2 shows a protective effect of the Lithospermi Radix extract (WLR) of the present invention on neurite growth in PC-2 cells which was induced by nerve growth factor (NGF) using a neurite outgrowth assay kit (N5225, Millipore).

As shown in FIG. 2 neurite growth of PC-12 cells induced by nerve growth factor (NGF) was observed. Nerve growth factor-induced neurite growth was inhibited by oxaliplatin (NGF+Oxal) and, such oxaliplatin-mediated inhibition of neurite growth was relieved by the Lithospermi Radix extract (NGF+Oxal+WLR) (FIG. 2).

2-2. Neuroprotective Effect of the Lithospermi Radix Extract—Quantitative Analysis For further in vitro determination of the neuroprotective effect of the Lithospermi Radix extract of the present invention, the neurite growth of PC-12 cells induced by nerve growth factor (NGF) was quantitatively analyzed.

Specifically, PC-12 cells cultured according to [Materials and Methods 3-1] were evenly plated at 1×10⁴ cells/well on a 24-well plate coated with collagen type IV in a DMEM growth medium where the cells were allowed to adhere on the bottom of the plate. After 12 hours, the medium was exchanged with a serum-free DMEM medium containing 100 ng/ml nerve growth factor (NGF) to induce neurite growth. The cells were treated with 200 nM oxaliplatin (Oxal) to induce neurotoxicity. Cells were co-treated with the Lithospermi Radix extract (WLR) prepared according to [Materials and Methods 1] at concentrations of 25 and 100 µg/ml, and amifostine (Ami) at 500 µM as a positive control.

After 3 days, the ratios of cells forming neurites and the lengths of the neurites were quantified using image analysis under an optical microscope.

As shown in FIGS. 3A and 3B, the neurite growth induced by nerve growth factor (NGF) was inhibited by oxaliplatin (NGF+Oxal+V), and such oxaliplatin-mediated inhibition of neurite growth was relieved by treatment of the Lithospermi Radix extract (WLR) (FIG. 3A). The ratio of cells forming neurites and the total relative lengths of growing neurites were increased by a Lithospermi Radix extract (FIG. 3B).

Example 3. Determination of the Protective Effect of the Lithospermi Radix Extract Against CIPN In Vivo The protective effect of the Lithospermi Radix extract against CIPN was determined by measuring mechanical allodynia in peripheral neuropathic animals induced by oxaliplatin.

Specifically, 2 weeks after pain induction in peripheral neuropathic animals according to [Materials and Methods 4], 250 mg/kg of the Lithospermi Radix extract (WLR) prepared according to [Materials and Methods 1] or 0.5% carboxymethyl cellulose (CMC) as a negative control was administered to animals 6 times per week for 4 weeks. In addition, 100 mg/kg of amifostine as a positive control, was intraperitoneally administered 2 times per week for 4 weeks. After pain induction for 2 weeks, von Frey filament test was carried out once a week during drug administration period by applying constant stimulation of 0.4 g to hind footpad of mouse. Sensitivity to the stimulation was expressed by frequency (%) of animals showing a response to the stimulation.

As shown in FIG. 4, the administration of oxaliplatin increased the paw sensitivity to stimulation of von Frey filament by about 35% to 75%. The enhanced sensitivity was maintained for 4 weeks even after termination of oxaliplatin administration. Co-treatment of the Lithospermi Radix extract effectively reduced the oxaliplain-mediated enhanced sensitivity to a basal level (i.e., 30 to 40%) consistently to the end point of the test (FIG. 4).

Example 4. Determination of the Neuroprotective Effect of the Lithospermi Radix Extract by Histological Analysis 4-1. Determination of the Neuroprotective Effect of the Lithospermi Radix Extract by Immunohistological Analysis The neuroprotective effect of the Lithospermi Radix extract was determined by observing the activation of glial cells in a spinal cord and nerve damages in the footpad skins of peripheral neuropathic animals induced by oxaliplatin.

Specifically, peripheral neuropathy was induced in male C57BL/6 mice by oxaliplatin (10 mg/kg) according to [Materials and Methods 4]. Then, the mouse was orally administered 6 times per week with 250 mg/kg of the Lithospermi Radix extract (WLR) prepared according to [Materials and Methods 1] or 0.5% carboxymethyl cellulose (CMC) as a negative control. In addition, 100 mg/kg amifostine was intraperitoneally administered 2 times per week as a positive control. After drug administration for 2 weeks, lumbar spinal cords and hind footpad skins were cut out according to [Materials and Methods 6-1]. Using the obtained specimen, activation of astrocytes and microglial cells in dorsal horn areas of the lumbar spinal cord of the animals was measured by detecting GFAP and Iba-1 marker proteins, respectively, according to [Materials and Methods 6-2]. Distribution of intraepidermal nerve fiber (IENF) in the hind footpad skin was measured by detecting PGP9.5 marker protein according to [Materials and Methods 6-3].

As shown in FIG. 5, the numbers of activated astrocytes (GFAP positive cells) and microglial cells (Iba-1 positive cells) were increased by oxaliplatin, which was reduced to the same extent in groups administered with Lithospermi Radix extract (WLR) and amifostine used as a positive control. It was also found that the densities of intraepidermal nerve fibers in hind footpad skin which was reduced by oxaliplatin, was recovered by both the Lithospermi Radix extract and amifostine. These results indicate that the Lithospermi Radix extract can reduce inflammation by glial cells and nerve damage in epidermal tissues caused by oxaliplatin (FIG. 5).

4-2. Determination of the Neuroprotective Effect of Lithospermi Radix Extract by Morphological Analysis of DRG Neurons Morphological changes in dorsal root ganglion (DRG) neurons caused by a Lithospermi Radix extract (WLR) was determined in peripheral neuropathic animals induced by oxaliplatin.

Specifically, peripheral neuropathy was induced in male C57BL/6 mice by oxaliplatin (10 mg/kg) according to [Materials and Methods 4]. After that, the mice were orally administered 6 times per week with 250 mg/kg of a Lithospermi Radix extract (WLR) prepared in [Materials and Methods 1] or 0.5% carboxymethyl cellulose (CMC) as a negative control. In addition, 100 mg/kg amifostine was intraperitoneally administered 2 times per week as a positive control. After drug administration for 2 weeks, dorsal root ganglion (DRG) was cut out according to [Materials and Methods 6-1]. Using the obtained specimen, morphological change of nucleus and nucleoli in the dorsal root ganglion (DRG) neurons was observed according to [Materials and Methods 6-4].

As shown in FIG. 6 the frequencies of DRG neurons having eccentric nucleoli, i.e., the nucleoli positioned in the periphery of the nucleus, and neurons having multinucleolated nucleus were increased by oxaliplatin treatment. Such morphological changes by oxaliplatin was reduced to the same extent in groups administered with a Lithospermi Radix extract (WLR) and amifostine used as a positive control. In particular, the number of neurons having multinucleolated nucleus was decreased with statistical significance. These results indicate that the Lithospermi Radix extract can alleviate inflammation in nerve tissues and pathological pains from peripheral neuropathic damages caused by oxaliplatin (Di Cesare Mannelli L, et al., 2013, Pain, v14, pp 1585-1600).

Example 5. Determination of In Vitro Cytotoxicity of the Lithospermi Radix Extract in Normal Cells Cytotoxicity of the Lithospermi Radix extract in human foreskin fibroblast cells was determined to see whether it is toxic to normal cells.

Specifically, human foreskin fibroblast cells were cultured according to [Materials and Methods 3-2]. The cells were plated in a 96-well culture dish at 2,000 cells per well. After 24 hours, the cells were treated with serially diluted Lithospermi Radix extract prepared according to [Materials and Methods 1] at final concentrations of 0 to 1000 µg/ml. After 48 hours, cell viability (%) was measured using Ez-Cytox assay kit (Daeillab Service Co., Ltd.). The relative cell viability (%) was calculated compared with the control group which was not treated with a Lithospermi Radix extract.

As shown in FIG. 7, the human foreskin fibroblast cells maintained their viability over 95% even when the cells were treated with a Lithospermi Radix extract at the maximum concentration of 1,000 μg/ml. Therefore, it was confirmed that the Lithospermi Radix extract is not toxic to normal cells (FIG. 7).

Example 6. In Vitro Evaluation of Drug-Herb Interaction Between the Lithospermi Radix Extract and Anti-Cancer Agent in Human Cancer Cells The effect of the Lithospermi Radix extract on cytotoxicity of anti-cancer agent was determined in vitro in human cancer cells to exclude a possibility that the Lithospermi Radix extract may affect negatively anti-cancer treatment when administered to a patient either simultaneously or sequentially in combination with an anti-cancer agent.

Specifically, human lung cancer cells (A549) and human colon cancer cells (HCT116) were cultured according to [Materials and Methods 3-3]. The cells were plated in a 96-well culture dish at 5,000 cells per well. After 24 hours, the cells were simultaneously treated with serially diluted oxaliplatin (0 to 100 μg/ml) and the Lithospermi Radix extract (0(PBS), 10, 30, 100 μg/ml) prepared according to [Materials and Methods 1]. The cell only treated with oxaliplatin was served as a negative control. After 72 hours, the cell viability (%) was measured using Ez-Cytox assay kit. The rate of cell death (% death) caused by oxaliplatin was expressed by (100−cell viability (%)).

As shown in FIG. 8, oxaliplatin (i.e., No treat) inhibited the growth of human lung (A549) and colon (HCT116) cancer cells in a dose-dependent manner. Co-treatment of the Lithospermi Radix extract at concentrations of 0 (or PBS physiological saline) to 100 μg/ml with oxaliplatin did not affect the efficacy of oxaliplatin to inhibit cancer cell growth (FIG. 8). Therefore, the Lithospermi Radix extract may not affect negatively the anti-cancer activity of oxaliplatin when clinically administered to a cancer patient in combination with oxaliplatin.

Example 7. Determination of the Effect of the Lithospermi Radix Extract on Activities of Human Drug Metabolism Enzyme (CYPs) and Drug Transporter (P-Gp)

When the Lithospermi Radix extract is to be co-administered with other general medication including an anti-cancer agent, there is a possibility of adverse side effect caused by drug interaction between the Lithospermi Radix extract and co-administered drug. The possible drug interaction can be predicted by determining the effect of drugs on the activity of drug metabolism enzymes. Accordingly, the inventors of the present invention determined the effect of the Lithospermi Radix extract on the activity and gene expression of a human drug metabolism enzyme. The study was performed for CYP which is responsible for most of drug metabolism, and P-gp protein as a drug transporter.

7-1. Determination of Inhibitory Effects of the Lithospermi Radix Extract on the Activities of CYPs and P-Gp In order to see whether a Lithospermi Radix extract inhibits the activities of CYP and P-gp, biochemical analyses were carried out according to [Materials and Methods 7-1].

Specifically, serially diluted Lithospermi Radix extract (WLR) prepared according to [Materials and Methods 1] was added to a reaction mixture containing each enzyme and substrate. The enzyme reaction was allowed to occur at specific temperature and time which were set for each enzyme. Luciferase enzyme reaction was initiated by adding detection reagent and the relative enzyme activity was determined by measuring the intensity of emitted luminescence.

As a result, the activity of all tested CYP were maintained at the level of 50% or higher when the Lithospermi Radix extract was increased up to 200 μg/ml (FIG. 9A). In particular no remarkable enzyme inhibition was observed in P-gp even when the Lithospermi Radix extract was increased to 1,000 μg/ml (FIG. 9A).

7-2. Determination of In Vitro Induction of Gene Expression of CYPs and P-Gp in Human Hepatoma Cell Line (HepaRG) by a Lithospermi Radix Extract In order to see whether the Lithospermi Radix extract modulates the gene expression of CYP and P-gp, in vitro tests were carried out using HepaRG, a human hepatoma cell line, according to [Materials and Methods 7-2].

Specifically, HepaRG cells cultured according to [Materials and Methods 3-4] were exposed for 24 hours to the Lithospermi Radix extract (10, 20, 100, 500 μg/ml) prepared according to [Materials and Methods 1]. Total intracellular RNA was extracted and cDNA was synthesized using total RNA as a template. Real-time PCR was carried out using the primers summarized in Table 1 and SYBR Green. The expression of target genes were relatively compared in HepaRG cells.

As a result, the expression of CYP1A2, CYP2B6, CYP3A4, and P-gp proteins was effectively enhanced by positive control drugs (i.e., omeprazole for CYP1A2 and CYP2B6, and rifampicin for CYP3A4 and P-gp) in HepaRG cells confirming that the in vitro system worked appropriately. In case of CYP3A4, the inhibition of gene expression was observed by the Lithospermi Radix extract at relatively high concentrations: by 65% at 100 μg/ml and by 75% at 500 μg/ml of Lithospermi Radix extract. Therefore, a caution might be clinically needed when the Lithospermi Radix extract is to be administered in combination with a medication including an anti-cancer drug that is metabolized by CYP3A4. In case of CYP1A2, CYP2B6, and P-gp, gene expression was not increased or decreased by 2 times or more even when the Lithospermi Radix extract was increased up to 500 μg/ml (FIG. 9B).

The invention claimed is:

1. A method for treating chemotherapy-induced peripheral neuropathy, the method comprising:
   administering to a subject in need thereof a composition comprising a Lithospermi Radix extract as an effective component.

2. The method of claim 1, wherein the extract is obtained by extraction using water, lower alcohol of $C_1$ to $C_4$, or a mixture thereof as a solvent.

3. The method of claim 2, wherein, the lower alcohol is methanol or ethanol.

4. The method of claim 1, wherein an anti-cancer agent for the chemotherapy is a platinum-based anti-cancer agent, a taxane-based anti-cancer agent, *vinca* alkaloid, bortezomib, thalidomide, or a combination thereof.

5. The method of claim 4, wherein the platinum-based anti-cancer agent is at least one selected from the group consisting of cisplatin, carboplatin, oxaliplatin, and a combination thereof.

6. The method of claim 4, wherein the anti-cancer agent is a platinum-based anti-cancer agent.

7. The method of claim 4, wherein the anti-cancer agent is oxaliplatin.

8. The method of claim 4, wherein the taxane-based anti-cancer agent is at least one selected from the group consisting of paclitaxel and docetaxel.

9. The method of claim 1, wherein the subject has received chemotherapy.

10. The method of claim 1, wherein the subject has been administered oxaliplatin.

11. The method of claim 1, wherein the composition is a pharmaceutical composition.

12. The method of claim 1, wherein the composition is a functional health food.

13. The method of claim 1, wherein the composition is an anti-cancer supplement.

14. A method for treating chemotherapy-induced peripheral neuropathy, the method comprising:
    administering to a subject a composition comprising a Lithospermi Radix extract as an effective component,
    wherein the subject has been administered one selected from the group consisting of a platinum-based anti-cancer agent, a taxane-based anti-cancer agent, *vinca* alkaloid, bortezomib, thalidomide, or a combination thereof; and
    the Lithospermi Radix extract comprises rosmarinic acid, lithospermic acid, salvianolic acid B, salvianolic acid A, and salvianolic acid C.

15. The method of claim 14, wherein the subject has been administered the platinum-based anti-cancer agent.

16. The method of claim 14, wherein the subject has been administered oxaliplatin.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence

```
<220> FEATURE:
<223> OTHER INFORMATION: primer

<400> SEQUENCE: 1
tgaatggctt ctacatcccc                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agggcttgtt aatggcagtg                                              20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
cccacacctc tgccttttt                                               19

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gcacaggctg ttgaccatc                                               19

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
ccccaaggac acagaagtat ttc                                          23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gattgaaggc gtctggtttt tc                                           22

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gccaaagcca aaatatcagc                                              20
```

```
<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ttccaatgtg ttcggcatta                                           20

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
aaggctgaga acgggaag                                             18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
ggactccacg acgtactc                                             18
```